(12) United States Patent
Billaud et al.

(10) Patent No.: US 12,371,402 B2
(45) Date of Patent: Jul. 29, 2025

(54) MITOCHONDRIAL ACTIVITY INHIBITORS TARGETING TUMORAL METABOLISM

(71) Applicants: CENTRE LEON BERARD, Lyons (FR); CENTRE NATIONAL DE LA RECHERCHE SCIENTIFIQUE (CNRS), Paris (FR); UNIVERSITE CLAUDE BERNARD LYON 1, Villeurbanne (FR); INSTITUT NATIONAL DE LA SANTE ET DE LA RECHERCHE MEDICALE (INSERM), Paris (FR); UNIVERSITE GRENOBLE ALPES, Saint Martin d'Heres (FR); UNIVERSITE DE CAEN NORMANDIE, Caen (FR)

(72) Inventors: Marc Billaud, Lyons (FR); Renaud Prudent, Renage (FR); Martine Cordier-Bussat, Chassieu (FR); Eric Fontaine, Bernin (FR); Patrick Dallemagne, Seulline (FR); Peggy Suzanne, Cairon (FR); Sylvain Rault, Moult (FR)

(73) Assignees: CENTRE LEON BERARD, Lyons (FR); CENTRE NATIONAL DE LA RECHERCHE SCIENTIFIQUE (CNRS), Paris (FR); UNIVERSITE CLAUDE BERNARD LYON 1, Villeurbanne (FR); INSTITUT NATIONAL DE LA SANTE ET DE LA RECHERCHE MEDICALE (INSERM), Paris (FR); UNIVERSITE GRENOBLE ALPES, Saint Martin d'Heres (FR); UNIVERSITE DE CAEN NORMANDIE, Caen (FR)

( * ) Notice: Subject to any disclaimer, the term of this patent is extended or adjusted under 35 U.S.C. 154(b) by 954 days.

(21) Appl. No.: 17/297,439

(22) PCT Filed: Nov. 28, 2019

(86) PCT No.: PCT/EP2019/082969
§ 371 (c)(1),
(2) Date: May 26, 2021

(87) PCT Pub. No.: WO2020/109506
PCT Pub. Date: Jun. 4, 2020

(65) Prior Publication Data
US 2022/0009884 A1    Jan. 13, 2022

(30) Foreign Application Priority Data

Nov. 28, 2018  (EP) .................................. 18306577

(51) Int. Cl.
*C07C 335/32*    (2006.01)
*A61P 35/00*     (2006.01)

(52) U.S. Cl.
CPC ............ *C07C 335/32* (2013.01); *A61P 35/00* (2018.01)

(58) Field of Classification Search
None
See application file for complete search history.

(56) References Cited

FOREIGN PATENT DOCUMENTS

| WO | 0107029 A2 | 2/2001 |
| WO | 2012047630 A2 | 4/2012 |

OTHER PUBLICATIONS

Djordjevic et al., Arteriosclerosis, Thrombosis, and Vascular Biology, vol. 25 519-525, 2005 (Year: 2005).*

(Continued)

*Primary Examiner* — Jeffrey S Lundgren
*Assistant Examiner* — Anthony Joseph Seitz
(74) *Attorney, Agent, or Firm* — Maier & Maier, PLLC

(57) ABSTRACT

The invention relates to compounds of formula (I) as follows: (I) wherein $X^1$ and $X^2$, identical or different, are $NR^5$ (Continued)

1A

1B

1C

1D or a sulfur atom, Y is a group $(C_1-C_{10})$alkanediyl, $Ar^1$ and $Ar^2$, identical or different, are an aryl group optionally substituted by one or several groups selected from a halogen atom, a $(C_1-C_6)$ alkyl, $-OR^1$, $-NR^1R^2$ and $-COOR^{3'}$ with $R^1$ and $R^2$, independently of each other, are a hydrogen atom, a $(C_{-1}-C_6)$ alkyl group or a $-COR^3$ group, $R^3$ and $R^{4'}$ independently of each other, are a hydrogen atom or a $(C_1-C_6)$ alkyl group, and $R^5$ is a hydrogen atom or a $(C_1-C_6)$alkyl group, or a pharmaceutically acceptable salt and/or solvate thereof, in particular for use in cancer treatment.

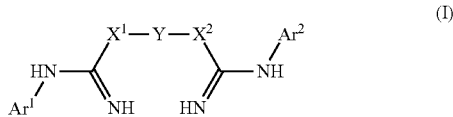

(I)

13 Claims, 8 Drawing Sheets

(56) References Cited

OTHER PUBLICATIONS

Wermuth CG. Drug Discov Today. Apr. 2006; 11(7-8):348-54 (Year: 2006).*
Shackelford et al., Nat Rev Cancer. Aug. 2009;9(8):563-75 (Year: 2009).*
Grieco et al., (2011), Urotensin II receptor predicts the clinical outcome of prostate cancer patients and is involved in the regulation of motility of prostate adenocarcinoma cells†‡. J. Cell. Biochem., 112: 341-353 (Year: 2011).*
Federico (Federico et al., Eur J Clin Invest 2014; 44 (3): 285-294 (Year: 2014).*
Wu et al., Expression of urotensin II and its receptor in human lung adenocarcinoma A549 cells and the effect of urotensin II on lung adenocarcinoma growth in vitro and in vivo . Oncol Rep 24: 1179-1184, 2010 (Year: 2010).*
Khalaf et al., European Journal of Medicinal Chemistry, vol. 45, Issue 4, 2010, pp. 1598-1617 (Year: 2010).*
Lescot et al., J. Chem. Inf. Model. 2007, 47, 2, 602-612 (Year: 2007).*
Saturnino C. et al., In vitro anti-acanthamoeba action by thioureidic derivatives, Il Farmaco, vol. 58, Issue 9, 2003, pp. 819-822.
Saturnino C. et al., Anti-oxidant activity of thioureidic derivatives I, Il Farmaco, vol. 58, Issue 9, 2003, pp. 823-828.
Communication issued on Dec. 21, 2023, in corresponding European Application No. 19816231.5, 5 pages.
Domanska U M et al., European Journal of Cancer 2013, 49, 219-230.
Abu Khalaf R et al., European Journal of Medicinal Chemistry 2010, 45, 1598-1617.
Saturnino C. et al. (2003)—In vitro anti-acanthamoeba action by thioureidic derivatives. Il Farmaco 2003, 58, p. 819-822.
Shepard J B et al., Anti-Cancer Drugs 2014, 25(1), 8-16.
Bardeesy N. et al. (2002)—Loss of the Lkb1 tumour suppressor provokesintestinal polyposis but resistance to transformation. Nature 2002, 419, 162-167.
Cordier-Bussat M. et al. (2018)—Même l'effet Warburg est oxydable; Coopération métabolique et développement tumoral. Médecine/sciences 2018, 34, 701-708.
Molina J. R. et al. (2018)—An inhibitor of oxidative phosphorylation exploits cancer vulnerability. Nature Medicine 2018, 24, 1036-1046.
Souroullas G.P. et al. (2017)—Lkb1 deletion in murine B lymphocytes promotes cell death and cancer. Exp Hematol 2017, 51, 63-70.
Berry M. N. and Friend D. S. (1969)—High-Yield Preparation of Isolated Rat Liver Parenchymal Cells—A Biochemical and Fine Structural Study. J. Cell Biol. 1969, 43, 506-520.
Groen A. K. et al. (1982)—Intracellular Compartmentation and Control of Alanine Metabolism in Rat Liver Parenchymal Cells. Eur. J. Biochem. 1982, 122, 87-93.

* cited by examiner

MITOCHONDRIAL ACTIVITY INHIBITORS TARGETING TUMORAL METABOLISM

FIELD OF THE INVENTION

The present invention relates to a family of compounds useful as mitochondrial electron chain transporter (ECT) complex 1 inhibitors (=ECT-1 inhibitors) for use in treatment of cancer.

BACKGROUND OF THE INVENTION

Cancers are a major cause of death around the world. Treatments of cancers are diverse. They include notably surgery, radiotherapy, chemotherapy, hormonotherapy, immunotherapy and targeted therapy.

However, there is still need to find new treatments, in particular in chemotherapy as side-effects of treatments can be significant or tumours can develop resistance mechanisms against chemotherapy.

It has been shown that reprogramming the energy metabolism is one of the key steps in the tumour development. Cancer cells can adapt to their microenvironment or selective pressure induced by chemotherapy treatments by adapting their metabolism. Notably, it has been discovered that cancer cells predominantly produce their energy through metabolization of glucose even in the presence of abundant oxygen and not by oxidative phosphorylation. This phenomenon of aerobic glycolysis, also called the Warburg effect, is less efficient than oxidative phosphorylation in terms of adenosine triphosphate production, but leads to the increased generation of additional metabolites that may particularly benefit proliferating cells. But recent observations prove that only ~20% of the total quantity of ATP is produced by glycolysis, the rest being largely due to mitochondrial oxidative phosphorylation (OXPHOS) activity (Martine Cordier-Bussat, 2018). Moreover, increased OXPHOS activity is often observed in tumoral cells resistant to chemotherapy. Thus, it is envisioned that blocking the respiratory chain and notably mitochondrial ECT-1 complex in tumors will lead to an energetic crisis of the cancer cells which will lead to their death. To this extent, mitochondrial ECT-1 inhibitors are envisioned as potential interesting cytotoxic agents. Metformin, an antidiabetic drug inhibiting this complex, has been shown to inhibit proliferation in several human cancers. However, this antiproliferative effect was observed at high concentrations of metformin, far higher than the concentrations authorized for its antidiabetic use. Metformin is therefore from now on more considered in combination with other cytotoxic agents or for the prevention of cancers.

There exists thus a need for novel mitochondrial ECT-1 inhibitors in cancer therapy, especially with higher potency and extended targets not limited as metformin by transport-mediated accumulation via OCT1 transporters.

The inventors have found compounds useful as mitochondrial ECT-1 inhibitors with cytotoxic and antiproliferative properties. It was demonstrated that they are cytotoxic on tumor cells at a concentration much lower than metformin (up to a thousand times less). They are more toxic on LKB1 deficient cells.

Additionally, it has been shown that such compounds immediately block oxygen consumption at lower concentrations in tumor cells than in normal cells. Moreover, they are well tolerated in animals and have antitumoral efficiency. Thus, a treatment using these compounds could be envisioned as a targeted therapy.

SUMMARY OF THE INVENTION

The present invention relates to compounds of formula (I) as follows:

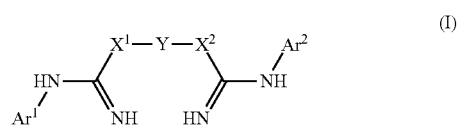

wherein
$X^1$ and $X^2$, identical or different, are $NR^5$ or a sulfur atom,
Y is a group $(C_1-C_{10})$alkanediyl,
$Ar^1$ and $Ar^2$, identical or different, are an aryl group optionally substituted by one or several groups selected from a halogen atom, $(C_1-C_6)$alkyl, $-OR^1$, $-NR^1R^2$ and $-COOR^3$,
with $R^1$ and $R^2$, independently of each other, are a hydrogen atom, a $(C_1-C_6)$alkyl group or a $-COR^4$ group,
$R^3$ and $R^4$, independently of each other, are a hydrogen atom or a $(C_1-C_6)$alkyl group, and
$R^5$ is a hydrogen atom or a $(C_1-C_6)$alkyl group,
or a pharmaceutically acceptable salt and/or solvate thereof,
for use in cancer treatment.

The present invention also relates to a pharmaceutical composition comprising a compound of formula (I) as defined above and at least one pharmaceutically acceptable excipient for use in cancer treatment.

The present invention also relates to a compound of formula (I) as follows:

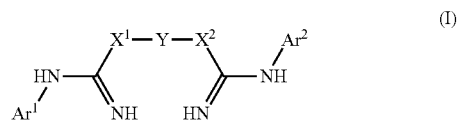

wherein
$X^1$ and $X^2$, identical or different, are $NR^5$ or a sulfur atom,
Y is a group $(C_1-C_{10})$alkanediyl,
$Ar^1$ and $Ar^2$, identical or different, are an aryl group optionally substituted by one or several groups selected from a halogen atom, $(C_1-C_6)$alkyl, $-OR^1$, $-NR^1R^2$ and $-COOR^3$,
with $R^1$ and $R^2$, independently of each other, are a hydrogen atom, a $(C_1-C_6)$alkyl group or a $-COR^4$ group,
$R^3$ and $R^4$, independently of each other, are a hydrogen atom or a $(C_1-C_6)$alkyl group, and
$R^5$ is a hydrogen atom or a $(C_1-C_6)$alkyl group,
or a pharmaceutically acceptable salt and/or solvate thereof.

DRAWINGS DESCRIPTION

FIG. 1A, SUDHL4 Diffuse Large B Cell Lymphoma (DLBCL): FIG. 1B, REC-1 Mantle Lymphoma: FIG. 1C, RL follicular Lymphoma: FIG. 1D) after incubation for 24 hours in the presence of different concentrations of compound 1 (grey squares) or of metformin (black circles).

FIG. 2A, HUT-78 Sesary T lymphoma: FIG. 2B, Karpas-384 gamma/delta PTCL lymphoma: FIG. 2C, SR-786 ALCL/Alk+ lymphoma: FIG. 2D) after incubation for 24 hours in the presence of different concentrations of compound 1 (grey squares) or of metformin (black circles).

Figure 4:
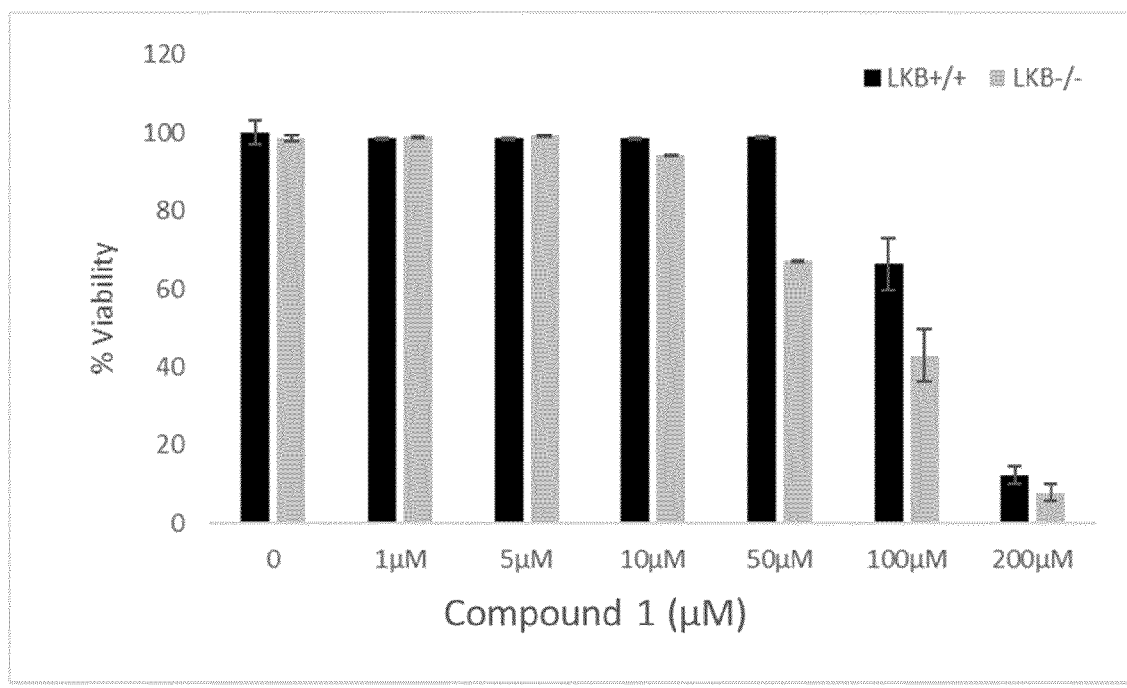

FIG. 4 represents the viability (expressed in percent) of cells LKB+/+ in black and cells LKB−/− in grey after incubation for 24 hours in the presence of different concentrations of compound 1 (0 µM, 1 µM, 5 µM, 10 µM, 50 µM, 100 µM and 200 µM respectively).

Figure 5:
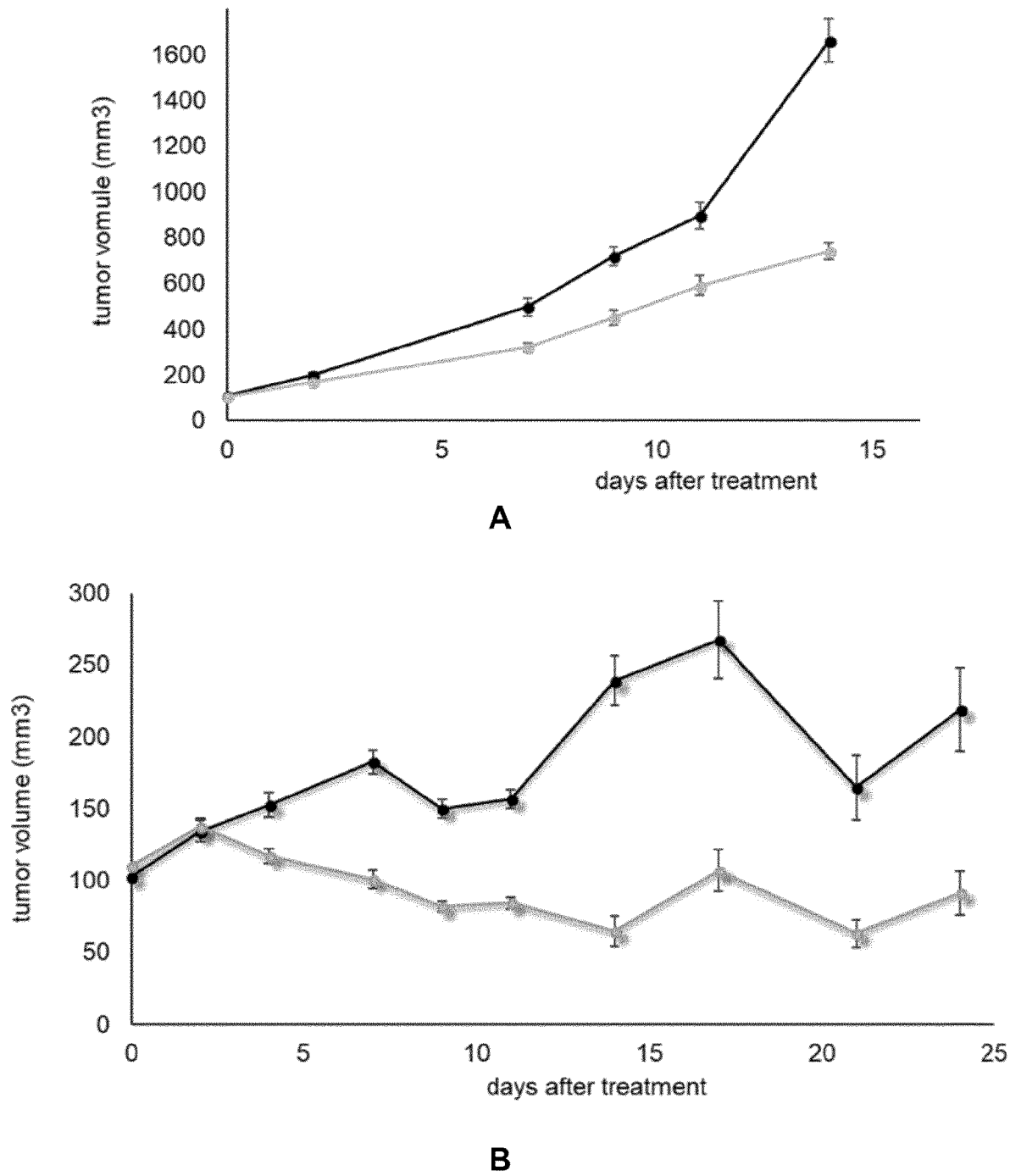

FIG. 5 represents the evolution of the tumor volume xenografts in mm$^3$ (RL follicular lymphoma xenograft: FIG. 5A, SUDFIL-4 lymphoma xenograft: FIG. 5B) on mice during the treatment of mice with 50 mg/kg of compound 1 (in grey) or with control excipient/DMSO (in black).

Figure 6A:
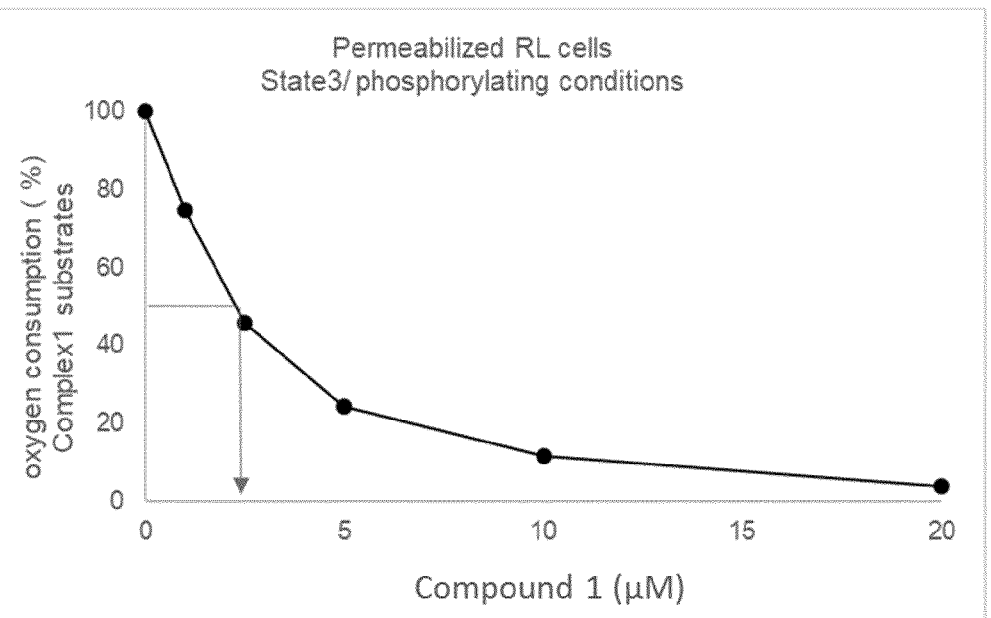
Figure 6B:
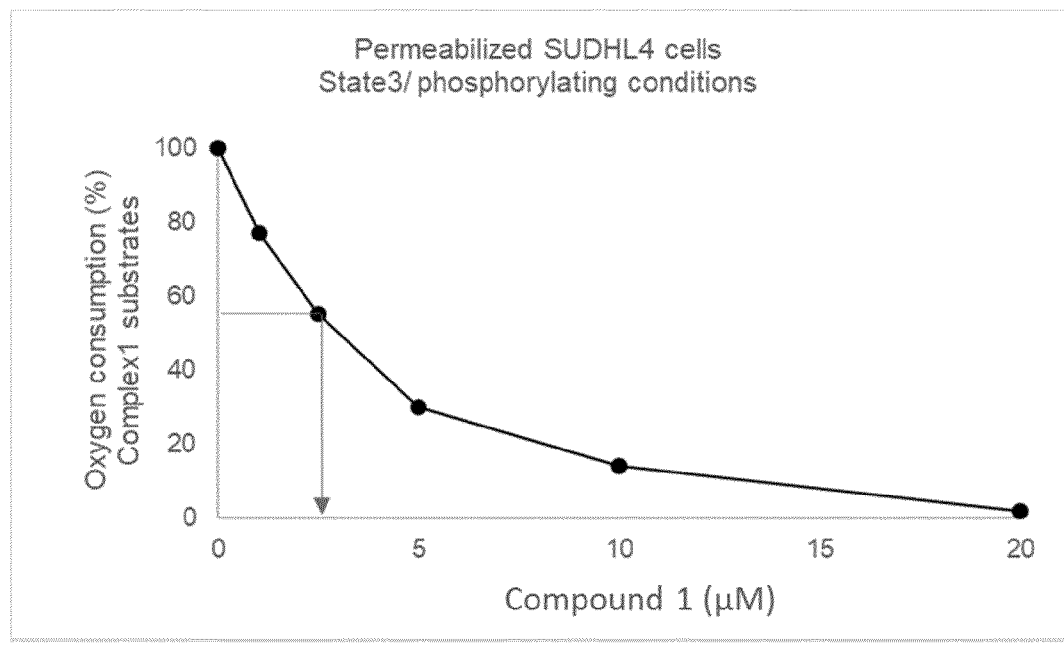
Figure 6C:
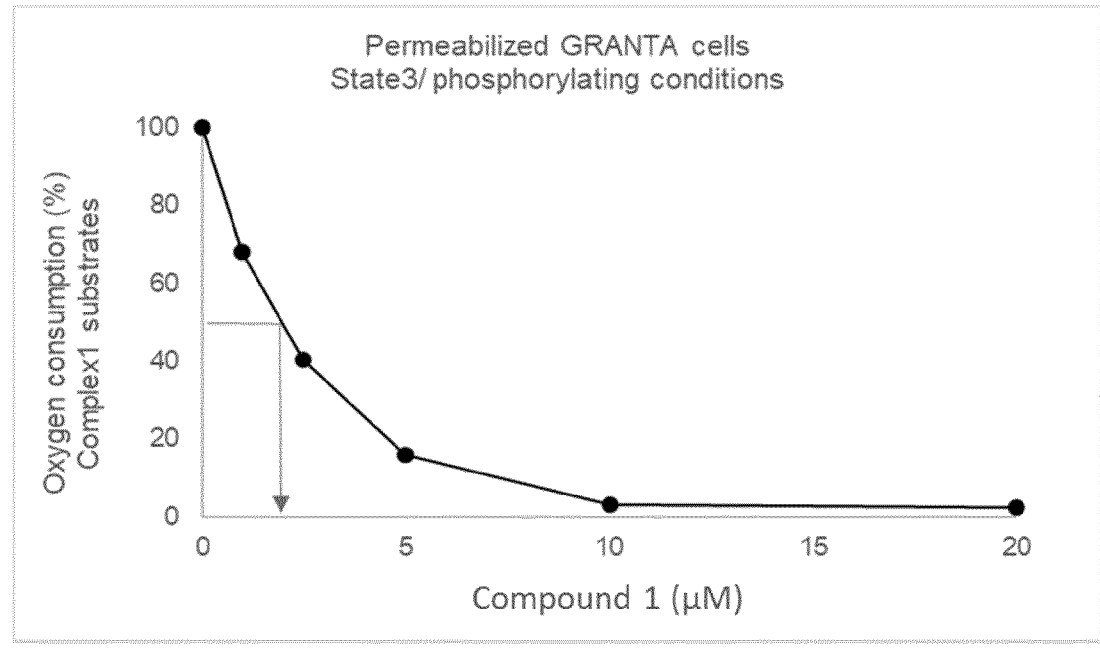
Figure 6D:
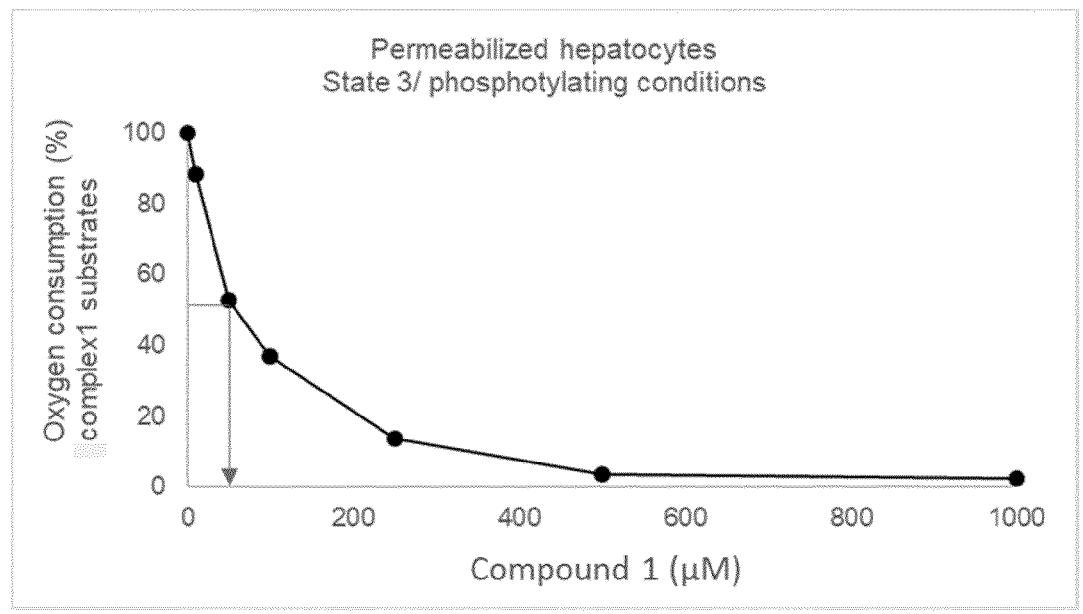

FIGS. 6A to 6D represent oxygen consumption (expressed in percent) of permeabilized cells (RL lymphoma cells: FIG. 6A, SUDFIL-4 lymphoma cells: FIG. 6B, GRANTA cells: FIG. 6C, rat liver hepatocytes: FIG. 6D) after 2 min in the presence of different concentrations of compound 1 (0 µM, 1 µM, 5 µM, 10 µM, 50 µM, 100 µM and 200 µM respectively).

Figure 7:
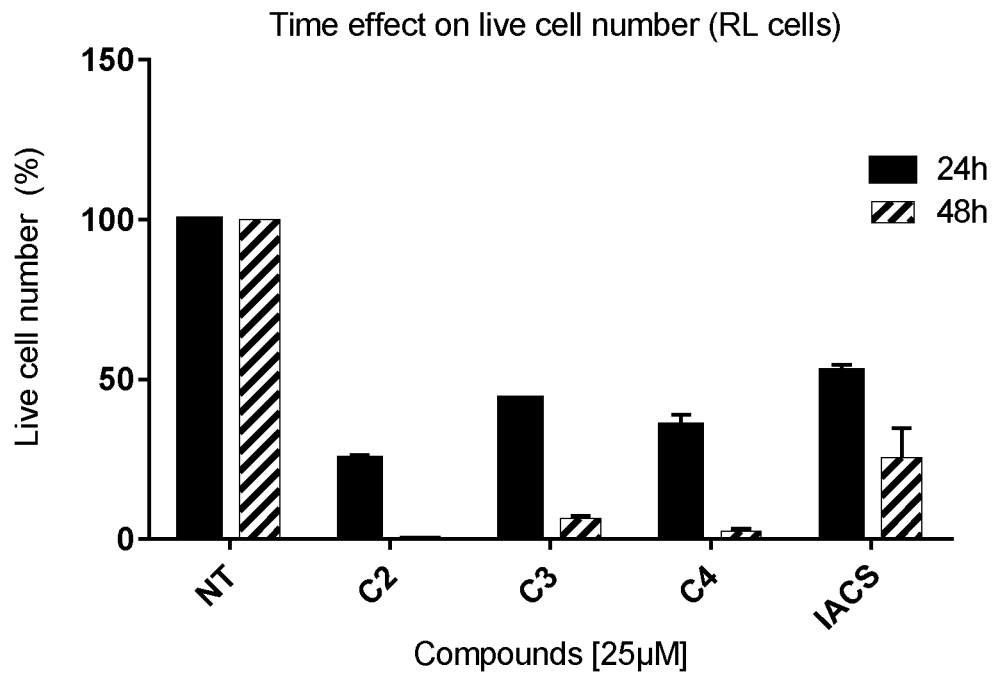

FIG. 7 represents live cell number (expressed in percent) of hematological cell line (RL follicular lymphoma) after incubation for 24 hours or 48 hours in the presence of 25 µM of different compounds (compounds 2 to 4-noted C2 to C4- and compound IACS) or in the absence of any compound (NT).

Figure 8:
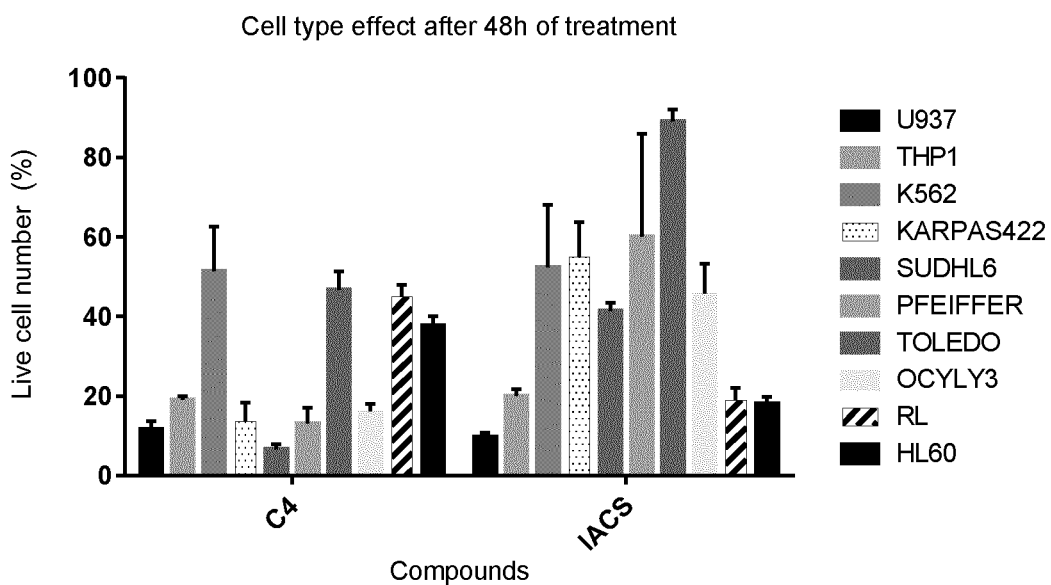

FIG. 8 represents live cell number (expressed in percent) of a panel of hematological cell lines (U937 histiolytic lymphoma (monocyte), THP1 acute monocytic leukemia, K562 leukemia, Karpas-422 DLBCL lymphoma, SUDHL-6 DLBCL lymphoma, PFEIFFER DLBCL lymphoma, TOLEDO DLBCL lymphoma, OCYLY3 DLBCL lymphoma, RL follicular lymphoma, HL60 leukemia) after incubation for 48 hours in the presence 10 µM of compound 4 (C4) or 10 µM of compound IACS.

Figure 9:
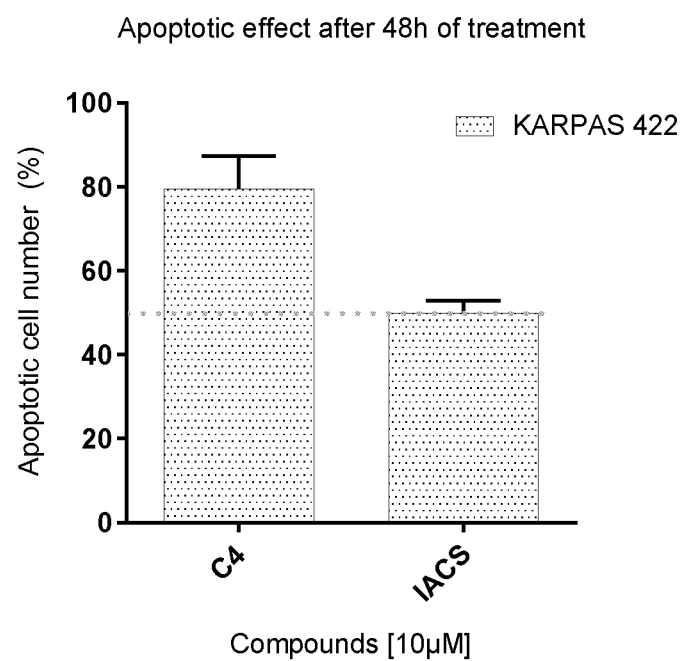

FIG. 9 represents apoptotic cells/cell decrease (expressed in percent) of hematological cell line Karpas-422 DLBCL lymphoma after incubation for 48 hours in the presence 10 µM of different compounds (compound 4 noted C4 and compound IACS).

DEFINITION

The term "$(C_1-C_{10})$alkanediyl", as used in the present invention, refers to a divalent a straight or branched saturated hydrocarbon chain containing from 1 to 10 carbon atoms including, but not limited to, methane-1,1-diyl, ethane-1,1-diyl, ethane-1,2-diyl, propane-1,3-diyl, butane-1,4-diyl, butane-1,3-diyl, butane-1,2-diyl, pentane-1,5-diyl, hexane-1,6-diyl, hexane-1,5-diyl, heptane-1,7-diyl, octane-1,8-diyl, nonane-1,9-diyl, decane-1,10-diyl and the like.

The term "aryl", as used in the present invention, refers to an aromatic hydrocarbon group comprising preferably 6 to 10 carbon atoms and comprising one or several fused rings, such as, for example, a phenyl or naphthyl group. Advantageously, it will be a phenyl group.

The term "halogen", as used in the present invention, refers to a fluorine, bromine, chlorine or iodine atom.

The term "$(C_1-C_6)$alkyl", as used in the present invention, refers to a monovalent straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as formic, acetic, benzenesulfonic, fumaric, glucoheptonic, gluconic, glutamic, glycolic, hydroxynaphthoic, 2-hydroxyethanesulfonic, lactic, maleic, malic, mandelic, methanesulfonic, muconic, 2-naphthalenesulfonic, propionic, succinic, dibenzoyl-L-tartaric, tartaric, p-toluenesulfonic, trimethylacetic, and trifluoroacetic acid and the like, and (2) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

DETAILED DESCRIPTION OF THE INVENTION

Compounds of formula (I) for use in cancer treatment:

The present invention relates to compounds of formula (I) as described above for use in cancer treatment.

According to a first embodiment, $X^1$ and/or $X^2$ is a sulfur atom.

According to a second embodiment, $X^1$ and/or $X^2$ is $NR^5$, preferably NH.

Advantageously, in these two embodiments, $X^1$ and $X^2$ are identical.

In particular, notably in these two embodiments, Y is a group —$(CH_2)_n$— and n is an integer between 1 and 10, preferably between 2 and 8, more preferably between 4 and 6.

Thus, $X^1$—Y—$X^2$ advantageously represents a chain of following formula: —S—$(CH_2)_n$—S—, —S—$(CH_2)_n$—$NR^5$—, —$NR^5$—$(CH_2)_n$—S—, or —$NR^5$—$(CH_2)_n$—$NR^5$—, preferably —S—$(CH_2)_n$—S— or —$NR^5$—$(CH_2)_n$—$NR^5$—, most preferably —S—$(CH_2)_n$—S— or —NH—

($CH_2$)$_n$—NH—, and even most preferably —S—($CH_2$)$_n$—S—, with n as defined above.

Advantageously, $Ar^1$ and/or $Ar^2$, preferably $Ar^1$ and $Ar^2$, is a phenyl or naphthyl group optionally substituted by one or several groups selected from an atom of halogen, —$OR^1$, —$NR^1R^2$, and —$COOR^3$.

Preferably, $Ar^1$ and/or $Ar^2$, preferably $Ar^1$ and $Ar^2$, is an unsubstituted aryl group, preferably an unsubstituted phenyl or naphthyl group.

In particular, $Ar^1$ and $Ar^2$ are identical.

According to a particular embodiment:
$X^1$—Y—$X^2$ represents a chain of following formula: —S—($CH_2$)$_n$—S—, —S—($CH_2$)$_n$—$NR^5$—, —$NR^5$—($CH_2$)$_n$—S—, or —$NR^5$—($CH_2$)$_n$—$NR^5$—, preferably —S—($CH_2$)$_n$—S—, —S—($CH_2$)$_n$—NH—, —NH—($CH_2$)$_n$—S—, or —NH—($CH_2$)$_n$—NH—, and most preferably —S—($CH_2$)$_n$—S—, with n as defined above; and $Ar^1$ and $Ar^2$ are, independently of one another, a phenyl or naphthyl group optionally substituted by one or several groups selected from an atom of halogen, —$OR^1$, —$NR^1R^2$, and —$COOR^3$.

According to another particular embodiment:
$X^1$—Y—$X^2$ represents a chain of following formula: —S—($CH_2$)$_n$—S— or —$NR^5$—($CH_2$)$_n$—$NR^5$—, preferably —S—($CH_2$)$_n$—S— or —NH—($CH_2$)$_n$—NH—, and most preferably —S—($CH_2$)$_n$—S—, with n as defined above; and $Ar^1$ and $Ar^2$ are identical and are a phenyl or naphthyl group optionally substituted by one or several groups selected from an atom of halogen, —$OR^1$, —$NR^1R^2$, and —$COOR^3$.

According to another particular embodiment:
$X^1$—Y—$X^2$ represents a chain of following formula: —S—($CH_2$)$_n$—S— or —$NR^5$—($CH_2$)$_n$—$NR^5$—, preferably —S—($CH_2$)$_n$—S— or —NH—($CH_2$)$_n$—NH—, and most preferably —S—($CH_2$)$_n$—S—, with n as defined above; and $Ar^1$ and $Ar^2$ are identical and are an unsubstituted aryl group, preferably a phenyl or naphthyl group.

Advantageously, the compound of formula (I) is selected from the group consisting of:

and the pharmaceutically acceptable salts and solvates thereof, preferably the hydrobromide salts thereof.

Preferentially, the compound of formula (I) is selected from the group consisting of:
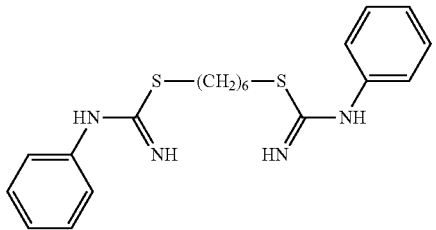
1
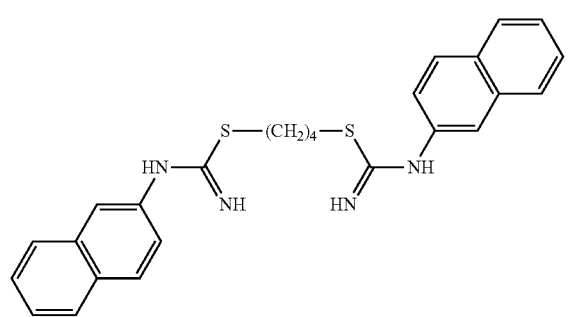
2
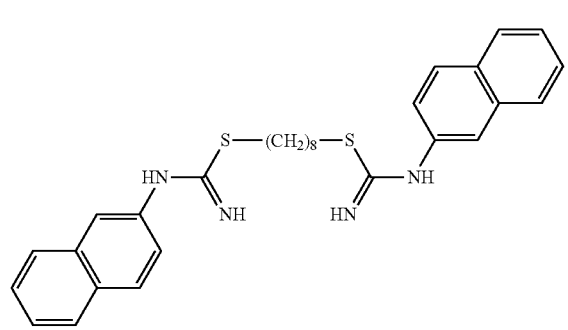
3
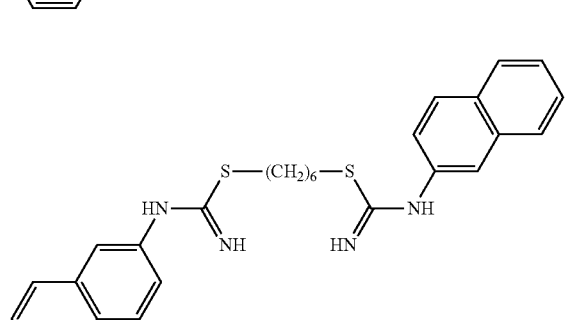
4
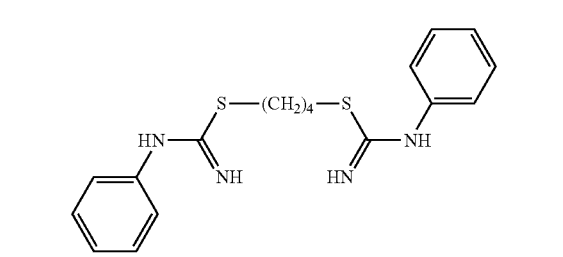
5
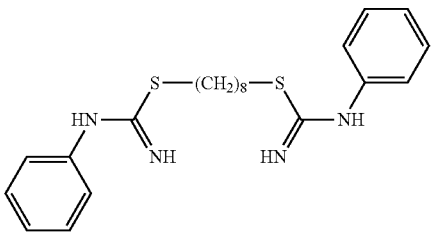
6
and the pharmaceutically acceptable salts and solvates thereof, preferably the hydrobromide salts thereof.
In particular, the compound of formula (I) is selected from the group consisting of:
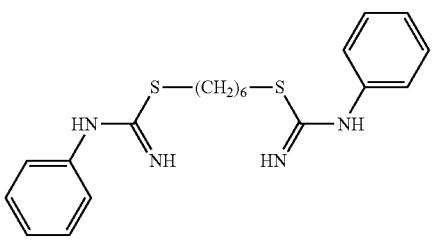
1
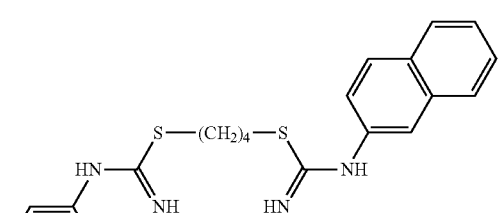
2
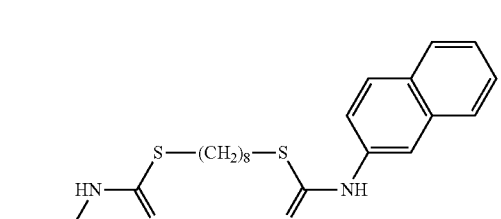
3

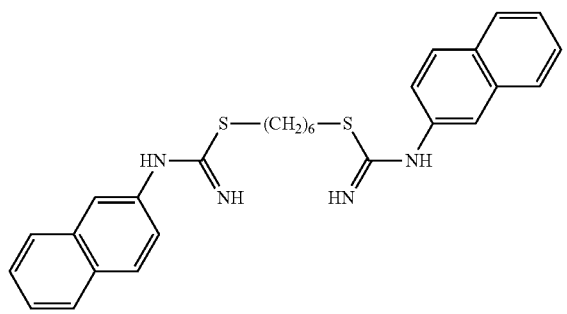

and the pharmaceutically acceptable salts and solvates thereof, preferably the hydrobromide salts thereof.

Compounds of formula (I) can be obtained as described in the article from (Saturnino et al., 2003)

The present invention relates to a compound of formula (I) or a pharmaceutically acceptable salt and/or solvate thereof as defined above, for use in the treatment of cancer.

The present invention also relates to the use of a compound of formula (I) or a pharmaceutically acceptable salt and/or solvate thereof as defined above, for the manufacture of a drug intended for the treatment of cancer.

The present invention also relates to a method for treating cancer comprising administering to a patient in need thereof an effective amount of a compound of formula (I) or a pharmaceutically acceptable salt and/or solvate thereof as defined above.

Preferably, the compounds of the present invention are used for treating cancers with modified metabolism, in particular cancers with OXPHOS metabolism.

A "cancer with OXPHOS metabolism" corresponds to a cancer which comprises or is constituted of cancer cells relying on OXPHOS for bioenergetics and/or biosynthetic processes.

In particular, the compounds of the present invention are used for treating a LKB-1 gene-deficient cancer.

LKB-1 gene, also known as STK11 gene encodes liver kinase B1 (LKB1) also known as serine/threonine kinase 11 (STK11), which is a protein kinase. LKB-1 gene-deficient cancer corresponds to a cancer which comprises or is constituted of cancer cells having a mutated or a deleted LKB-1 gene.

Among the cancers to be treated, haematological cancers, lung cancers, cervix cancers, prostate cancer, melanoma and neuroendocrine tumours can be cited.

In particular, the haematological cancers to be treated can be leukaemia, lymphoma or myeloma, more particularly lymphoma, notably non-Hodgkin lymphomas (NHL).

Preferably, melanoma, prostate, lung and/or cervix cancers to be treated are LKB-1 gene-deficient cancers.

Advantageously, the cancers to be treated resulting from neuroendocrine tumors are pancreatic cancers.

Preferably, the cancers to be treated are lymphoma, notably non-Hodgkin lymphomas (NHL).

Advantageously, cancers to be treated are selected among the group consisting of B-cell lymphoma and T-cell lymphoma.

In particular, the patient in need of a treatment is a mammal, notably a human.

Advantageously, the compounds of the present invention can be used to treat cancer by acting as inhibitors of the mitochondrial ECT-1.

The compounds can be used alone or in combination, advantageously synergetic, with at least another active compound.

The present invention also relates to a method for inhibiting the mitochondrial ECT-1 comprising administering to a patient in need thereof an effective amount of a compound of formula (I) or a pharmaceutically acceptable salt and/or solvate thereof as defined above.

Pharmaceutical Compositions:

The present invention also relates to a pharmaceutical composition comprising a compound of formula (I) as defined above and at least one pharmaceutically acceptable excipient for use in cancer treatment.

The pharmaceutical composition according to the invention can further comprise at least another active compound, other than the compounds according to the invention.

The present invention also relates to the use of a pharmaceutical composition as defined above, for the manufacture of a drug intended for the treatment of cancer.

The present invention also relates to a method for treating cancer comprising administering to a patient in need thereof an effective amount of a pharmaceutical composition as defined above.

Preferably, the cancers are cancers with modified metabolism, in particular cancers with OXPHOS metabolism.

In particular, the cancers can be LKB-1 gene-deficient cancers.

Among the cancers to be treated, haematological cancers, lung cancers, cervix cancers, prostate cancer, melanoma and neuroendocrine tumors can be cited.

In particular, the haematological cancers to be treated can be leukemia, lymphoma or myeloma, more particularly lymphoma, notably non-Hodgkin lymphomas (NHL).

Preferably, melanoma, prostate, lung and/or cervix cancers to be treated are LKB-1 gene-deficient cancers.

Advantageously, the cancers to be treated resulting from neuroendocrine tumors are pancreatic cancers.

Preferably, the cancers to be treated are lymphoma, notably non-Hodgkin lymphomas (NHL).

Advantageously, cancers to be treated are selected among the group consisting of B-cell lymphoma and T-cell lymphoma.

In particular, the patient in need of a treatment is a mammal, notably a human.

Advantageously, the pharmaceutical composition of the present invention can be used to treat cancer by acting as inhibitors of the mitochondrial ECT-1.

The present invention also relates to a method for inhibiting the mitochondrial ECT-1 comprising administering to a patient in need thereof an effective amount of a pharmaceutical composition as defined above.

The active ingredient(s) of the pharmaceutical composition according to the invention (comprising at least one compound of formula (I) or a pharmaceutically acceptable salt and/or solvate thereof) may be administered in unit dosage forms of administration, in mixture with standard pharmaceutical carriers, to animals, in particular mammals, including humans. The pharmaceutical compositions according to the invention may be formulated notably for oral administration or parenteral administration (e.g. intravenous injection).

For oral administration, the pharmaceutical composition can be in a solid or liquid (solution or suspension) form.

A solid composition can be in the form of tablets, gelatin capsules, powders, granules and the like. In tablets, the active ingredient can be mixed with pharmaceutical vehicle(s) such as gelatin, starch, lactose, magnesium stearate, talc, gum arabic and the like before being compressed. The tablets may be coated, notably with sucrose or with other suitable materials, or they may be treated in such a way that they have a prolonged or delayed activity. In powders or granules, the active ingredient can be mixed or granulated with dispersing agents, wetting agents or suspending agents and with flavour correctors or sweeteners. In gelatine capsules, the active ingredient can be introduced into soft or hard gelatine capsules for example in the form of a powder or granules, such as mentioned previously.

A liquid composition can contain the active ingredient together with a sweetener, a taste enhancer or a suitable colouring agent in a solvent such as water. The liquid composition can also be obtained by suspending or dissolving a powder or granules, as mentioned above, in a liquid such as water, juice, milk, etc. It can be for example a syrup or an elixir.

For parenteral administration, the composition can be in the form of an aqueous suspension or solution, which may contain dispersing agents and/or wetting agents. The composition is advantageously sterile. It can be in the form of an isotonic solution (in particular in comparison to blood).

The compounds of the invention as active ingredients may be used in doses ranging between 0.01 mg and 1000 mg per day, given in a single dose once per day or administered in several doses throughout the day, for example twice a day in equal doses. The dose administered per day advantageously is between 5 mg and 500 mg, even more advantageously between 10 mg and 200 mg. It may be necessary to use doses outside these ranges as determined by the person skilled in the art.

Compounds:

The present invention also relates to a compound of formula (I) as described above or a pharmaceutically acceptable salt and/or solvate thereof.

In particular, the compounds according to the invention are not:

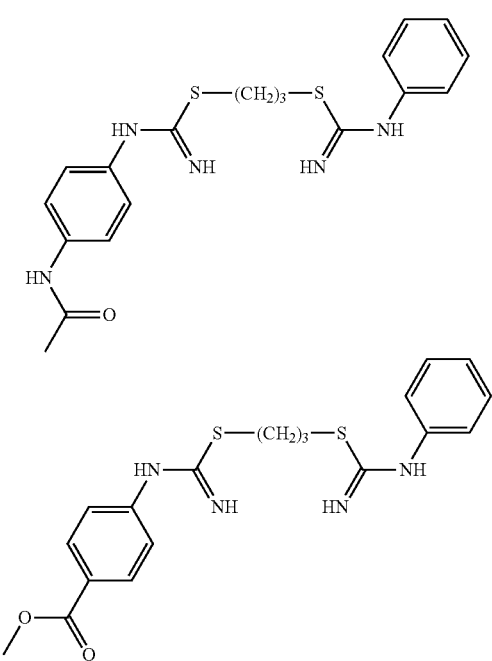

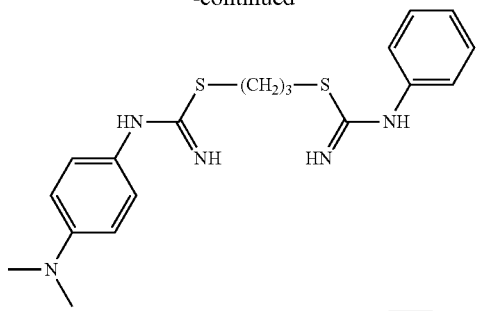

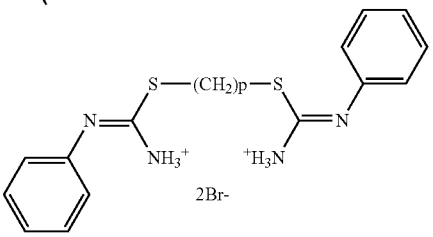

with p = 3, 4, 5, 6, 7, 8, 9

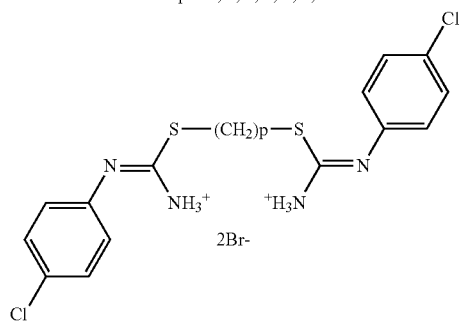

with p = 4, 5, 6, 7, 8, 9

These compounds are disclosed in US 2013/0143961 or in Saturnino et al. *Il Farmaco* 2003, 58, 819-822. However, no biological result in the treatment of cancer is reported in these documents.

According to a first embodiment, $X^1$ and/or $X^2$ is a sulfur atom.

According to a second embodiment, $X^1$ and/or $X^2$ is $NR^5$, preferably NH.

Advantageously, in these two embodiments, $X^1$ and $X^2$ are identical, more advantageously $X^1$ and $X^2$ are sulfur atoms.

In particular, notably in these two embodiments, Y is a group $-(CH_2)_n-$ and n is an integer between 1 and 10, preferably between 2 and 8, more preferably between 4 and 6.

Thus, $X^1-Y-X^2$ advantageously represents a chain of following formula: $-S-(CH_2)_n-S-$, $-S-(CH_2)_n-NR^5-$, $-NR^5-(CH_2)_n-S-$, or $-NR^5-(CH_2)_n-NR^5-$, preferably $-S-(CH_2)_n-S-$ or $-NR^5-(CH_2)_n-NR^5-$, most preferably $-S-(CH_2)_n-S-$ or $-NH-(CH_2)_n-NH-$, and even most preferably $-S-(CH_2)_n-S-$, with n as defined above.

Advantageously, $Ar^1$ and/or $Ar^2$, preferably $Ar^1$ and $Ar^2$, is a phenyl or naphthyl group, in particular a naphthyl group, optionally substituted by one or several groups selected from an atom of halogen, $-OR^1$, $-NR^1R^2$, and $-COOR^3$.

Preferably, $Ar^1$ and/or $Ar^2$, preferably $Ar^1$ and $Ar^2$, is an unsubstituted aryl group, preferably an unsubstituted phenyl or naphthyl group, more preferably an unsubstituted naphthyl group.

In particular, $Ar^1$ and $Ar^2$ are identical.

According to a particular embodiment:
X¹—Y—X² represents a chain of following formula: —S—(CH₂)ₙ—S—, —S—(CH₂)ₙ—NR⁵—, —NR⁵—(CH₂)ₙ—S—, or —NR⁵—(CH₂)ₙ—NR⁵—, preferably —S—(CH₂)ₙ—S—, —S—(CH₂)ₙ—NH—, —NH—(CH₂)ₙ—S—, or —NH—(CH₂)ₙ—NH—, and most preferably —S—(CH₂)ₙ—S—, with n as defined above; and
Ar¹ and Ar² are, independently of one another, a phenyl or naphthyl group, in particular a naphthyl group, optionally substituted by one or several groups selected from an atom of halogen, —OR¹, —NR¹R², and —COOR³.

According to another particular embodiment:
X¹—Y—X² represents a chain of following formula —S—(CH₂)ₙ—S—, with n as defined above; and
Ar¹ and Ar² are, independently of one another, a naphthyl group optionally substituted by one or several groups selected from an atom of halogen, —OR¹, —NR¹R², and —COOR³.

According to another particular embodiment:
X¹—Y—X² represents a chain of following formula: —S—(CH₂)ₙ—S— or —NR⁵—(CH₂)ₙ—NR⁵—, preferably —S—(CH₂)ₙ—S— or —NH—(CH₂)ₙ—NH—, and most preferably —S—(CH₂)ₙ—S—, with n as defined above; and
Ar¹ and Ar² are identical and are a phenyl or naphthyl group, in particular a naphthyl group, optionally substituted by one or several groups selected from an atom of halogen, —OR¹, —NR¹R², and —COOR³

According to another particular embodiment:
X¹—Y—X² represents a chain of following formula —S—(CH₂)ₙ—S—, with n as defined above; and
Ar¹ and Ar² are identical and are a naphthyl group optionally substituted by one or several groups selected from an atom of halogen, —OR¹, —NR¹R², and —COOR³.

According to another particular embodiment:
X¹—Y—X² represents a chain of following formula: —S—(CH₂)ₙ—S— or —NR⁵—(CH₂)ₙ—NR⁵—, preferably —S—(CH₂)ₙ—S— or —NH—(CH₂)ₙ—NH—, and most preferably —S—(CH₂)ₙ—S—, with n as defined above; and
Ar¹ and Ar² are identical and are an unsubstituted aryl group, preferably a phenyl or naphthyl group, in particular a naphthyl group.

According to another particular embodiment:
X¹—Y—X² represents a chain of following formula —S—(CH₂)ₙ—S—, with n as defined above; and
Ar¹ and Ar² are an unsubstituted naphthyl group.

Advantageously, the compound of formula (I) is selected from the group consisting of:

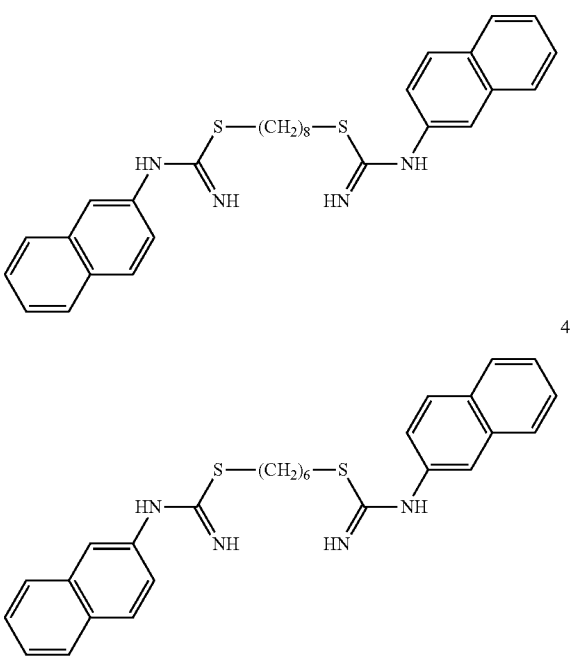

and the pharmaceutically acceptable salts and solvates thereof, preferably the hydrobromide salts thereof.

EXAMPLES

For examples 1 and 2:
RL cells (from ATCC, CRL-2261), SUDHL-4 cells (from ATCC, CRL-2957), GRANTA cells, BJAB Burkitt lymphoma cells, SUDHL4 DLBCL lymphoma cells, REC-1 Mantle lymphoma cells, RL follicular lymphoma cells, MTA NK/T lymphoma cells, HUT-78 Sesary T lymphoma cells, Karpas-384 gamma/delta PTCL lymphoma cells and SR-786 ALCL/Alk+ lymphoma Wild type/rescue MEF_LKB1+/+(mouse embryonic fibroblasts) cells were taken as a control; and mutated MEF_LKB−/− cells in which LKB1 gene was invalidated (Bardeesy et al., 2002). All cells were grown in flasks in RPMI 1640 Glutamax medium 11 mM Glucose supplemented with 10% fetal bovine serum and 1% penicillin-streptomycin medium supplemented with 10% fetal bovine serum and 1% penicillin-streptomycin. Cells were maintained at a constant temperature of 37° C. in a humidified atmosphere containing 5% CO₂/95% air.

Drugs (compound 1 and Metformin) were initially diluted in DMSO (=vehicle dimethylsulfoxide). Appropriate dilutions of these stocks were performed in DMSO and finally in culture medium; 15 µl of each dilution was distributed in 4 wells (replicates) according to the plate schedule to obtain final drug concentrations (0.1 µM to 1 mM for metformin and 1 µM to 200 µM for compound 1) after cells were added. Control wells with vehicle at the appropriate dilution only were included. Lymphoma cells in exponential phase of growth were counted and assessed for more than 95% viability by trypan blue coloration. There were seeded at 30000 cells/well in a volume of 35 µl of fresh RPMI culture medium/11 mM glucose/10% FCS, in the above 384 well plates containing the drugs. Adherent cells (MEFs cells and INS-1 cells were seeded the day before to obtain 80% confluence the day of experiment. Culture medium was renewed with 35 µL fresh medium and 15 µl of appropriated drug dilution was then added. These plates were incubated 24 hours at 37° C./5% $CO_2$. Then addition of 5 µl of WST-1 cell proliferation reagent (Roche, #11644807001) was performed, before incubation 2-4 hours at 37° C. and lecture of the absorbance following the manufacturer instructions. WST-1 assays are non-radioactive, rapid and more sensitive than MTT, XTT, or MTS-based assays. The WST-1 assay is based on the cleavage of the tetrazolium salt WST-1 to formazan by cellular mitochondrial dehydrogenases. Expansion in the number of viable cells results in an increase in the activity of the mitochondrial dehydrogenases, which in turn leads to increase in the amount of formazan dye formed. The formazan dye produced by viable cells can be quantified by measuring the absorbance at 440 nm. Cell viability was assessed comparing wells containing drugs to those with vehicle only. Cytotoxicity was confirmed by annexin V detection by FACS analysis, and by CytoTox 96® Promega test.

Example 1: Comparative Effect of Compound 1 on Human Lymphoma Cell Lines

Figure 1:
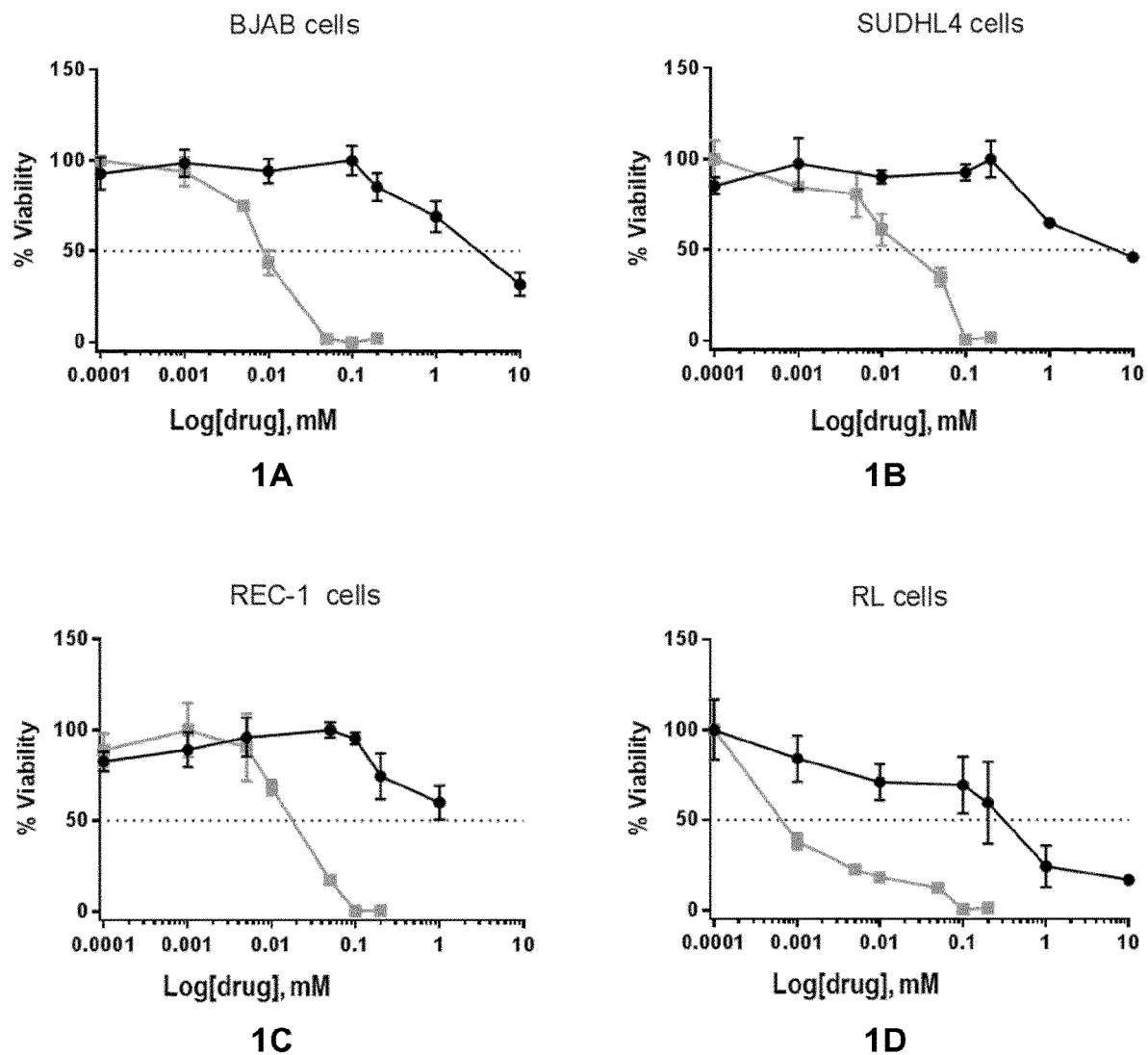
FIG. 1 represents the viability (expressed in percent) of Human B lymphoma cell lines (BJAB Burkitt lymphoma.
Figure 2:
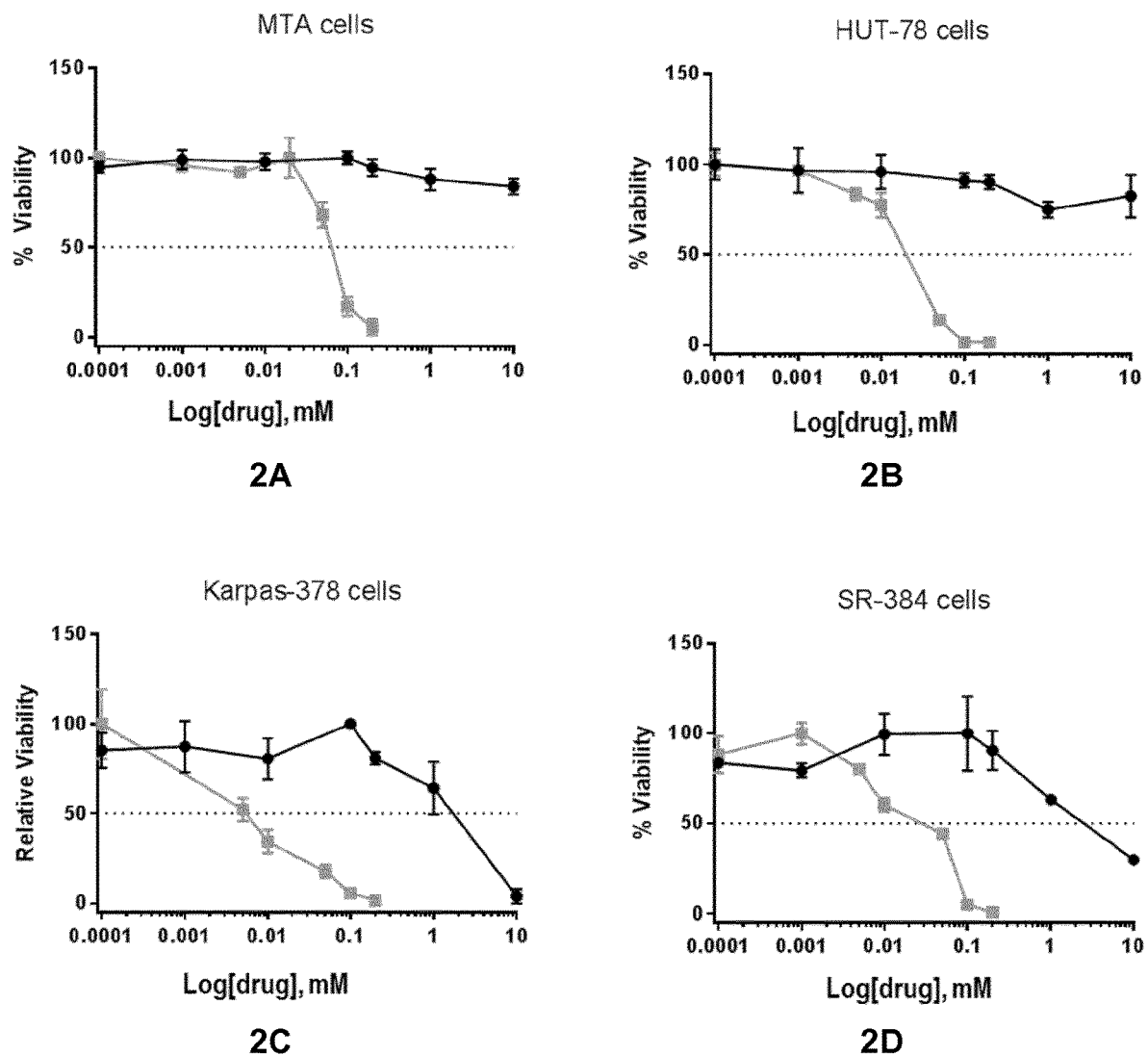
FIG. 2 represents the viability (expressed in percent) of Human T lymphoma cell lines (MTA NK/T lymphoma.

Cells were incubated 24 hours in the presence of increasing concentration of the drug (6 doses from 1 µM to 200 µM) before the WST-1 test evaluating cell viability was performed. The % of viability compared to the cells not treated with the drug (0) is shown. Results are illustrated in FIGS. 1 and 2.

Human B lymphoma as well as human T lymphoma are sensible to compound 1. In particular, IC50 of compound 1 is below 10 µM for RL and Karpas-384 lymphoma. In all lymphomas, IC50 of compound 1 is far below IC50 of metformin.

Example 2: Comparative Effect of Compound 1 on Pancreatic Tumour Cell Line

Cells were incubated 24 hours in the presence of increasing concentration of the drug (6 doses from 1 µM to 200 µM) before the WST-1 test evaluating cell viability was performed.

The % of viability compared to the cells not treated with the drug (0) is shown.

Figure 3:
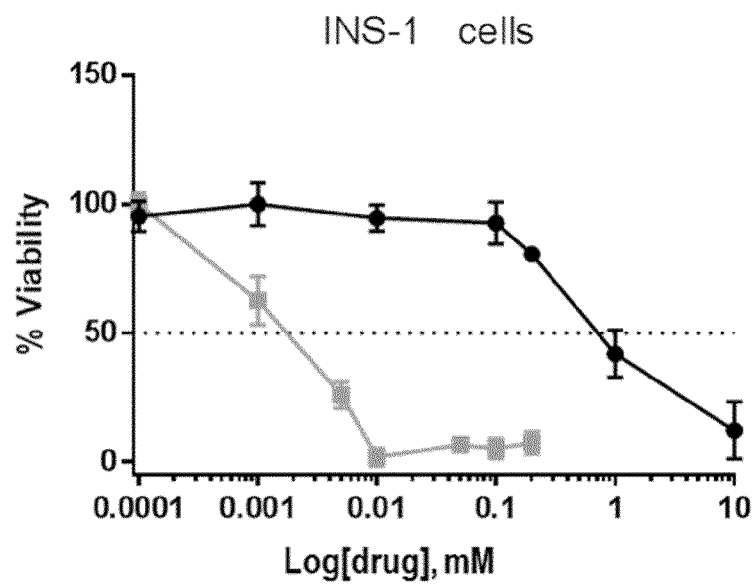
FIG. 3 represents the viability (expressed in percent) of pancreatic neuroendocrine tumor cell line INS-1 after incubation for 24 hours in the presence of different concentrations of compound 1 (grey squares) or of metformin (black circles).

Results are illustrated in FIG. 3.

Neuroendocrine pancreatic tumor (INS-1 cells) is sensible to compound 1. In particular, IC50 of compound 1 is below 10 µM and is far below IC50 of metformin.

Example 3: Comparative Effect of Compound 1 on Cells with or without the LKB1 Gene Mutated MEF_LKB–/– cells (mouse embryonic fibroblasts) in which LKB1 gene was genetically invalidated were used and MEF_LKB1+/+(previous cells in which LKB1 gene was stably re expressed) were taken as a control (Bardeesy et al., 2002).

Cells were incubated 24 hours in the presence of increasing concentration of the drug (6 doses from 1 µM to 200 µM) before the WST-1 test evaluating cell viability was performed.

The % of viability compared to the cells not treated with the drug (0) is shown. Results are illustrated in FIG. 4.

Compound 1 is more toxic for the cells that do not express the LKB1 protein.

Example 4: Effect of Compound 1 In Vivo on Human Cells Xenographs

CDX (cell derived xenografts) models of human NHL were used: Follicular Lymphoma (RL model), Diffuse Large B Cell Lymphoma (SUDHL-4 model). Cells were subcutaneously implanted; since the tumor growth was not homogeneous, it was decided to implant surgically 2×2 mm pieces from these initial tumours. Animals were female SCID mice.

Mice were randomized when the tumors reach a mean volume of 100 $mm^3$ for the 2 groups (control and compound 1). All the mice were observed in order to detect any toxic effects of the product. The endpoints are defined by animal ethics as a tumor diameter of >18 mm, significant weight loss or alteration of animal well-being. In order to assess the effectiveness of the compound 1 on tumorigenesis, tumor volume was measured three times a week. The sizes of the primary tumors were measured using calipers and the tumor volume (TV) was extrapolated to a sphere using the formula TV=4/3 π×r3, by calculating the mean radius from the two measurements. The median and standard deviation were also calculated for each group. Median is preferred to mean in order to exclude the extreme values.

COMPOUND 1 was administered by intraperitoneal injection five times a week, at dose 50 mg/kg. Control DMSO was administered also by intraperitoneal injection five times a week. Mice were sacrificed when the tumors reached a maximum volume of 1600 $mm^3$. The endpoints are defined by clinical trial ethics as a tumor diameter of >18 mm or weight loss of >10% of body weight, or when the tumors are dangerous for mice (necrosis).

Unless specified, the non-parametric Mann-Whitney test was performed on the tumor volume values ($mm^3$) measured on the day of the first euthanasia.

Results are illustrated in FIG. 5.

COMPOUND 1 treatment reduces tumor growth on two CDX models of human lymphoma.

Example 5: Compound 1 Inhibits Mitochondrial ECT-1 Function

Human Cell lines: RL cells (from ATCC, CRL-2261) and SU-DHL-4 cells (from ATCC, CRL-2957) were grown in flasks in RPMI 1640—Glutamax medium supplemented with 10% fetal bovine serum and 1% penicillin-streptomycin. GRANTA cells were grown in flasks in DMEM-Glutamax medium supplemented with 10% fetal bovine serum and 1% penicillin-streptomycin. Cells were maintained at a constant temperature of 37° C. in a humidified atmosphere containing 5% $CO_2$/95% air.

Hepatocyte Isolation:

Rat liver hepatocytes were isolated from overnight-starved animals by enzymatic digestion with collagenase according to the method of Berry and Friend modified by Groen.

Primary hepatocytes were directly used after isolation (for metabolic analyses). Cells were maintained at a constant temperature of 37° C. in a humidified atmosphere containing 5% $CO_2$/95% air. The medium was removed after 4 h (time necessary for cell attachment) and replaced by fresh medium.

Measurement of Oxygen Consumption in Permeabilized Cells:

Oxygen consumption was measured in a thermostatically controlled oxigraph vessel equipped with a Clarck oxygen electrode at 37° C. (Strathkelvin MS200A system).

Experiment was started by the addition of 100 μg/ml digitonine and either 5 mM Glutamate plus 2.5 mM Malate or 5 mM Succinate plus 1 μM rotenone, followed by the addition of 500 μM ADP (state 3) then 2 μg/ml Oligomycin (state 4).

Primary hepatocytes: 5.105 fresh hepatocytes were added in the oxigraph chamber containing respiration buffer (KET buffer: KCl 125 mM, EGTA 1 mM, Tris 20 mM) supplemented with 0.1% BSA, 5 mM inorganic phosphate (Pi). The final volume was 1 ml. Oxygen consumption rate was measured before and after the addition of compound 1 (1, 20, 50 or 100 μM) either in resting (state 2) or phosphorylating (state 3) condition.

Cell lines: RL, SU-DHL-4 or GRANTA cells were centrifuged and counted. A cell suspension (100 million of trypan blue negative cells per ml) was prepared in respiration buffer. 10 million cells were added in the oxigraph chamber containing respiration buffer. The final volume was 1 ml. compound 1 (0.5 to 20 μM) was added to permeabilized cells after the addition of ADP or oligomycin.

All measures were realized 2 min after drugs addition.

Results in the phosphorylating conditions (state 3) are illustrated in FIGS. 6A to 6D.

Compound 1 inhibits mitochondrial oxygen consumption in all cells tested; this activity is mostly dependent on the mitochondrial ECT complex1, and not on ECT complex2. Moreover, this effect of compound 1 is dose dependent. Remarkably, the dose necessary to inhibit oxygen consumption on permeabilized tumoral cells (RL, SUDHL4 and GRANTA cell lines) is about 25 times smaller than the dose inhibiting oxygen consumption on permeabilized fresh hepatocytes. This observation suggests higher toxicity of compound 1 on the tumoral mitochondria versus normal cell mitochondria. Indeed, in permeabilized cells, isolated mitochondria activity is evaluated, independently of cell integrity: cytoplasmic factors etc. since plasma membrane is destroyed by digitonin treatment.

Example 6: Comparative Analysis of the Toxicity of Compounds 2 to 4 by Flow Cytometry on a Series of Human Hematological Lines All the cells were routinely maintained in RPMI 1640 culture medium 11 mM glucose supplemented with 10% FCS. The day of experiment, cells (80 to 100.10³/well) in exponential phase of growth were seeded in 96 wells plates, in 100 μl of culture medium final volume, in absence (not treated: NT) or presence of indicated compounds concentrations. Stocks of compounds were 10 mM in DMSO, and final DMSO concentration in assay was 0.1%. The control not treated (NT) assays contains 0.1% DMSO. After 48h of incubation at 37° C., cells were immediately analyzed by flow cytometry. Apoptosis was detected using Annexin V/PI staining protocol, according to manufacturer indications.

Compounds 2 to 4 (named respectively C2 to C4 in the figures) were tested and compared with IACS-010759 (IACS), an OXPHOS inhibitor in clinical phase 1 trial which is assessed in parallel (Molina et al., 2018).

Results are illustrated in FIGS. 7 to 9.

As shown in FIG. 7, we observe a decrease in the number of living cells after 24 hours which is amplified after 48 hours of treatment with compounds 2 to 4.

As shown in FIG. 8, we observe that compound 4 induces a differential decrease in the number of living cells after 48 hours of treatment.

As illustrated by FIG. 9, we observe that compound 4 can induce apoptosis.

REFERENCES

Bardeesy, N., Sinha, M., Hezel, A. F., Signoretti, S., Hathaway, N. A., Sharpless, N. E., Loda, M., Carrasco, D. R., and DePinho, R. A. (2002). Loss of the Lkb1 tumour suppressor provokes intestinal polyposis but resistance to transformation. Nature 419, 162-167.

Martine Cordier-Bussat, C. T., Pierre Sujobert, Laurent Genestier, Éric Fontaine, Marc Billaud (2018). Même l'effet Warburg est oxydable; Cooperation mêtabolique et developpement tumoral, mêdecine/sciences 34, 701-708.

Molina, J. R., Sun, Y., Protopopova, M., Gera, S., Bandi, M., Bristow, C., McAfoos, T., Morlacchi, P., Ackroyd, J., Agip, A. A., et al. (2018). An inhibitor of oxidative phosphorylation exploits cancer vulnerability. Nat Med 24, 1036-1046.

Saturnino, C., Buonerba, M., Paesano, N., Lancelot, J. C., and De Martino, G. (2003). In vitro anti-acanthamoeba action by thioureidic derivatives. Farmaco 58, 819-822.

Souroullas, G. P., Fedoriw, Y., Staudt, L. M., and Sharpless, N. E. (2017). Lkb1 deletion in murine B lymphocytes promotes cell death and cancer. Exp Hematol 51, 63-70 e61.

Berry, M. N., and Friend, D. S. (1969) J. Cell Biol. 43, 506-520.

Groen, A. K., Sips, H. J., Vervoorn, R. C., and Tager, J. M. (1982) Eur. J. Biochem. 122, 87-93.

Molina, J. R., Sun, Y., Protopopova, M. et al. An inhibitor of oxidative phosphorylation exploits cancer vulnerability. Nat Med 24, 1036-1046 (2018)

The invention claimed is:

1. A method for treating a cancer comprising administering to a patient in need thereof an effective amount of a compound of formula (I) as follows:

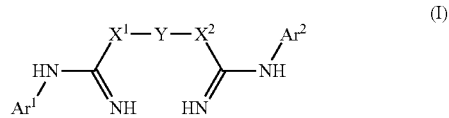

wherein
$X^1$ and $X^2$, identical or different, are $NR^5$ or a sulfur atom, and at least one of $X^1$ and $X^2$ is a sulfur atom,
Y is a group $(C_1$-$C_{10})$ alkanediyl,
$Ar^1$ and $Ar^2$, identical or different, are each a naphthyl group optionally substituted by one or several groups selected from a halogen atom, a $(C_1$-$C_6)$ alkyl, —$OR^1$, —$NR^1R^2$ and —$COOR^3$,
with $R^1$ and $R^2$, independently of each other, are a hydrogen atom, a $(C_1$-$C_6)$ alkyl group or a —$COR^4$ group,
$R^3$ and $R^4$, independently of each other, are a hydrogen atom or a $(C_1$-$C_6)$ alkyl group, and
$R^5$ is a hydrogen atom or a $(C_1$-$C_6)$ alkyl group,
or a pharmaceutically acceptable salt and/or solvate thereof.

2. The method according to claim 1, wherein Y is a group —$(CH_2)_n$— and n is an integer between 1 and 10.

3. The method according to claim 1, wherein $X^1$ and $X^2$ are a sulfur atom.

4. The method according to claim 1, wherein $Ar^1$ and $Ar^2$ are identical.

5. The method according to claim 1, wherein Ar¹ and/or Ar² is an unsubstituted naphthyl group.

6. The method according to claim 1, wherein the compound of formula (I) is selected from the group consisting of:

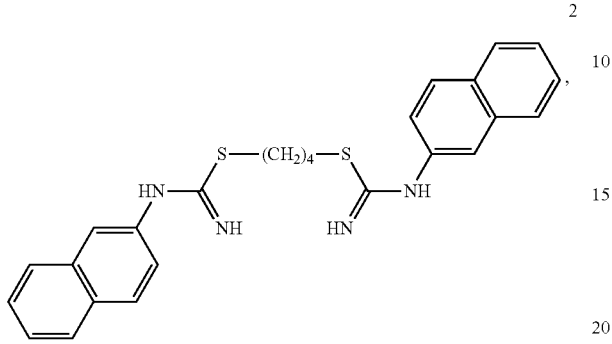

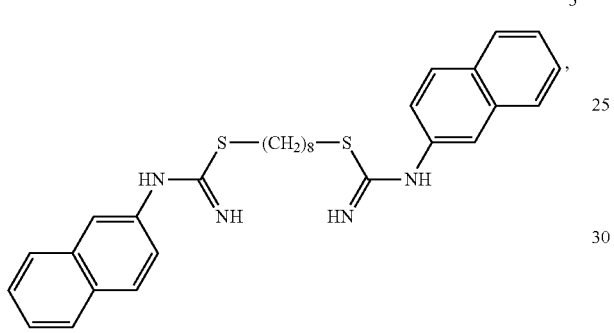

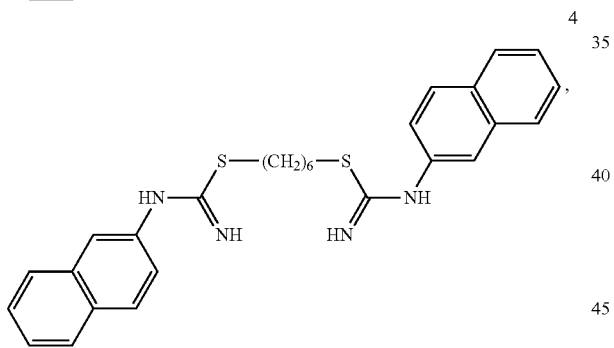

and the pharmaceutically acceptable salts and solvates thereof.

7. The method according to claim 1, wherein the cancer is selected from the group consisting of haematological cancers, lung cancers, cervix cancers, prostate cancer, melanoma and neuroendocrine tumors.

8. The method according to claim 1, wherein the cancer is a LKB-1 gene-deficient cancer.

9. A method for treating a cancer comprising administering to a patient in need thereof an effective amount of a pharmaceutical composition comprising a compound of formula (I) as defined in claim 1 and at least one pharmaceutically acceptable excipient.

10. The method according to claim 9, wherein the cancer is selected from the group consisting of haematological cancers, lung cancers, cervix cancers, prostate cancer, melanoma and neuroendocrine tumors.

11. The method according to claim 9, wherein the cancer is a LKB-1 gene-deficient cancer.

12. A method for inhibiting mitochondrial complex I, comprising administering to a patient in need thereof an effective amount of a compound of formula (I) as follows:

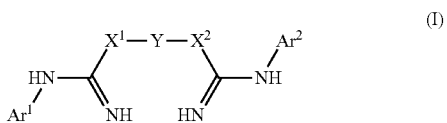

wherein $X^1$ and $X^2$, identical or different, are $NR^5$ or a sulfur atom, and at least one of $X^1$ and $X^2$ is a sulfur atom, Y is a group $(C_1\text{-}C_{10})$ alkanediyl, $Ar^1$ and $Ar^2$, identical or different, are each a naphthyl group optionally substituted by one or several groups selected from a halogen atom, a $(C_1\text{-}C_6)$ alkyl, $-OR^1$, $-NR^1R^2$ and $-COOR^3$, with $R^1$ and $R^2$, independently of each other, are a hydrogen atom, a $(C_1\text{-}C_6)$ alkyl group or a $-COR^4$ group, $R^3$ and $R^4$, independently of each other, are a hydrogen atom or a $(C_1\text{-}C_6)$ alkyl group, and $R^5$ is a hydrogen atom or a $(C_1\text{-}C_6)$ alkyl group, or a pharmaceutically acceptable salt and/or solvate thereof or a composition comprising said compound of formula (I) and at least one pharmaceutically acceptable excipient.

13. A compound selected from the group consisting of:

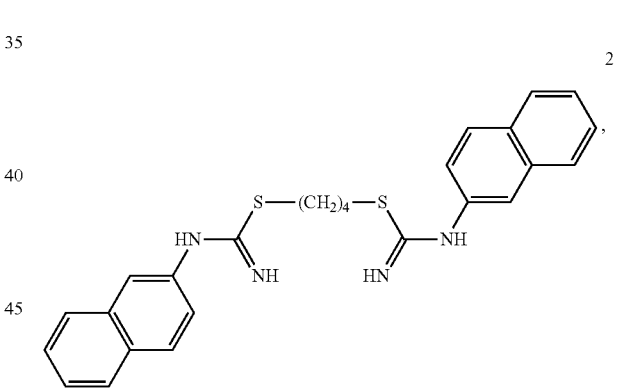

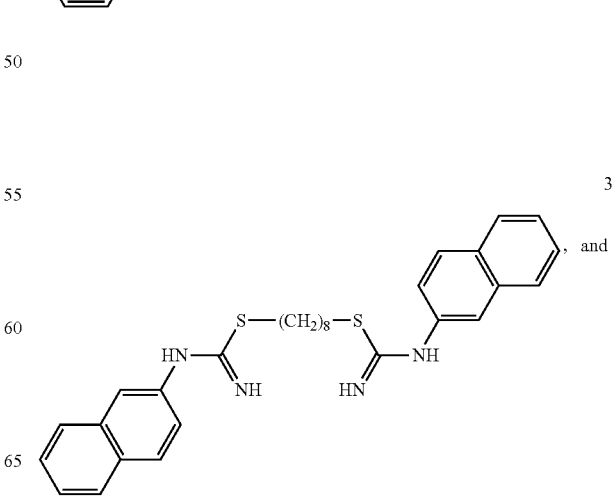

-continued
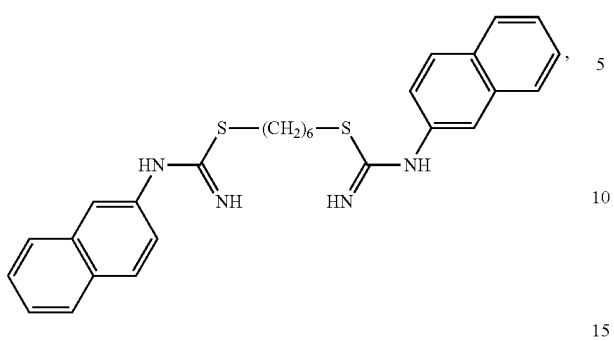
and the pharmaceutically acceptable salts and solvates thereof.
* * * * *